(12) United States Patent
Aoki et al.

(10) Patent No.: US 11,333,626 B2
(45) Date of Patent: May 17, 2022

(54) BIOLOGICAL SAMPLE ANALYSIS CHIP, BIOLOGICAL SAMPLE ANALYZER AND BIOLOGICAL SAMPLE ANALYSIS METHOD

(71) Applicant: HITACHI, LTD., Tokyo (JP)

(72) Inventors: Mayu Aoki, Tokyo (JP); Kenichi Takeda, Tokyo (JP); Kunio Harada, Tokyo (JP)

(73) Assignee: HITACHI, LTD., Tokyo (JP)

(*) Notice: Subject to any disclaimer, the term of this patent is extended or adjusted under 35 U.S.C. 154(b) by 652 days.

(21) Appl. No.: 16/070,602

(22) PCT Filed: Feb. 22, 2016

(86) PCT No.: PCT/JP2016/055096
§ 371 (c)(1),
(2) Date: Jul. 17, 2018

(87) PCT Pub. No.: WO2017/145239
PCT Pub. Date: Aug. 31, 2017

(65) Prior Publication Data
US 2019/0022647 A1 Jan. 24, 2019

(51) Int. Cl.
*G01N 27/447* (2006.01)
*B01L 3/00* (2006.01)
(Continued)

(52) U.S. Cl.
CPC .. *G01N 27/44791* (2013.01); *B01L 3/502715* (2013.01); *G01N 27/4145* (2013.01);
(Continued)

(58) Field of Classification Search
CPC ........ C12Q 2565/631; C12Q 2563/157; C12Q 1/002; G01N 33/48728; G01N 27/3335;
(Continued)

(56) References Cited

U.S. PATENT DOCUMENTS

2006/0240543 A1  10/2006  Folch et al.
2009/0194429 A1   8/2009  Hibbs et al.
(Continued)

FOREIGN PATENT DOCUMENTS

JP   2009-540332 A   11/2009
JP   2012-026986 A    2/2012
(Continued)

OTHER PUBLICATIONS

Japanese Office Action received in corresponding Japanese Application No. 2018-501428 dated Dec. 18, 2019.
(Continued)

*Primary Examiner* — Dean Kwak
(74) *Attorney, Agent, or Firm* — Mattingly & Malur, PC (57) ABSTRACT

A biological sample analysis chip including a first substrate, a membrane disposed on the first substrate, a first liquid tank which is provided with a first electrode, a plurality of second liquid tanks each of which is provided with at least one flow path and a second electrode; and a second substrate disposed below the first substrate, in which the plurality of second liquid tanks are substantially insulated from each other, the membrane disposed on the first substrate is disposed between the first liquid tank and the plurality of second liquid tanks so as to form a portion of the first liquid tank and a portion of the plurality of second liquid tanks, and the second substrate is provided with the at least one flow path and the second electrode so as to form a portion of the plurality of second liquid tanks.

7 Claims, 7 Drawing Sheets

(51) Int. Cl.
*G01N 27/414* (2006.01)
*G01N 33/543* (2006.01)

(52) U.S. Cl.
CPC . *B01L 2200/027* (2013.01); *B01L 2300/0636* (2013.01); *B01L 2300/0645* (2013.01); *B01L 2400/0421* (2013.01); *G01N 27/447* (2013.01); *G01N 33/54373* (2013.01)

(58) Field of Classification Search
CPC ........... G01N 27/40; G01N 2001/4016; G01N 27/4145; G01N 33/54373; B01L 2400/0421; B01L 2200/027; B01L 2300/0636; B01L 2300/0645; B01L 3/502715
See application file for complete search history.

(56) References Cited

U.S. PATENT DOCUMENTS

| | | | |
|---|---|---|---|
| 2013/0180867 A1* | 7/2013 | Rosenstein | B82Y 5/00 205/777.5 |
| 2014/0158540 A1* | 6/2014 | Ohura | G01N 27/44791 204/543 |
| 2014/0374255 A1 | 12/2014 | Hongo et al. | |
| 2016/0327513 A1 | 11/2016 | Yanagi et al. | |

FOREIGN PATENT DOCUMENTS

| | | |
|---|---|---|
| WO | 2013/137209 A1 | 9/2013 |
| WO | 2014/064443 A2 | 5/2014 |
| WO | 2015/097765 A1 | 7/2015 |

OTHER PUBLICATIONS

Changbae Hyun et al., "Threading Immobilized DNA Molecules through a Solid-State Nanopore at>100 μS per Base Rate", ACS Nano, Jul. 23, 2013, vol. 7, No. 7, pp. 5892-5900.
Kazuma Matsui et al., "Preventionof Dielectric Breakdown of Nanopore Membranes by Charge Neutralization, Scientific Reports", Dec. 4, 2015, vol. 5, 17819.
International Search Report of PCT/JP2016/055096 dated Apr. 26, 2016.

* cited by examiner

BIOLOGICAL SAMPLE ANALYSIS CHIP, BIOLOGICAL SAMPLE ANALYZER AND BIOLOGICAL SAMPLE ANALYSIS METHOD

TECHNICAL FIELD

The present invention relates to a biological sample analysis chip, a biological sample analyzer, and biological sample analysis method.

BACKGROUND ART

A blockage current type nanopore sequencer has been developed as a biological sample analyzer that analyzes biological samples such as DNA and protein.

The blockage current type nanopore sequencer is formed of a thin membrane having pores of approximately the same size as a biological sample and a liquid tank having electrodes arranged above and below the membrane. In such a configuration, the liquid tank is filled with a solution, and the biological sample is introduced from one side of the liquid tank. In addition, a voltage is applied to the electrodes, and a change in a current value flowing between the electrodes when the biological sample passes through the pores is measured. With such a measurement, structural features of the biological sample are determined.

Currently, a method of forming the blockage current type nanopore sequencer generally has two types such as "biological type" and "solid-state type". The biological type is a method of using biological molecules. In the biological type, first, a membrane on which an amphiphilic lipid bilayer membrane is placed is disposed in the liquid tank filled with the solution. Then, pores are formed by floating a modified protein (such as Mycrobacterium smegmatis porin A) having nanometer-sized pores on the membrane of the lipid bilayer membrane. The biological type has a problem in that the protein and the lipid bilayer membrane to be used are likely to be denatured. Accordingly, a solid-state type in which the biomolecules are not used has been expected.

The solid-state type is a technique of using a material with high mechanical strength and a process. In the solid-state type, for example, a silicon nitride film is used as a membrane, and the nanometer-sized pores are formed in the membrane by irradiation with an electron beam or application of a voltage.

One problem in the nanopore sequencer is that reading accuracy is low, a reading speed needs to be slow in order to improve the accuracy, and the same structure needs to be read a plurality of times, and improving a throughput as a single sequencer is difficult. Therefore, it is effective means to arrange a plurality of nanopore sequencers in an array and measure the structure of the biomolecules in parallel. In the arrayed structure of the nanopore sequencers, it is necessary to parallelize not only the pores but also peripheral structures such as accompanying liquid tanks, electrodes and the like.

Regarding the biological type nanopore sequencer, development of a configuration in which the sequencers are arrayed has been made progress. For example, PTL 1 discloses a parallelization method of a liquid tank in the biological type. In PTL 1, a plurality of independent liquid tanks are formed by replacing a surplus of the polar liquid which is continuous between parallel wells with a nonpolar liquid, and a membrane formed of the amphiphilic lipid bilayer membrane is self-organized afterwards in a nonpolar liquid layer sandwiched with a polar liquid.

On the other hand, in a general solid-state type nanopore sequencer, a material having the high mechanical strength typified by a silicon nitride film is formed on a substrate, and then the silicon nitride film is exposed by forming an opening in the substrate. With this, a substrate having a membrane is formed. In addition, a member constituting the liquid tank is attached above and below the substrate having the membrane. At least two flow paths (for example, a flow path for introducing a solution and a flow path for discharging a gas existing in the liquid tank and extra liquid) are provided in the liquid tank.

For example, PTL 2 discloses arraying of a solid-state type nanopore sequencer. PTL 2 discloses a structure in which one of two flow paths connected to a liquid tank also serves as an electrode.

CITATION LIST

Patent Literature

PTL 1: WO2014/064443
PTL 2: JP-A-2012-26986

SUMMARY OF INVENTION

Technical Problem

With regard to a method of PTL 1, unless a material of the membrane is provided with fluidity and amphiphilicity, it is impossible to provide a membrane between the liquid tanks arranged above and below. In the solid-state type nanopore sequencer, the material having the high mechanical strength typified by the silicon nitride film is used as a membrane, the method of PTL 1 cannot be applied to the solid-state type nanopore sequencer.

In a case of performing the arraying of the solid-state type nanopore sequencer, it is necessary that components (a liquid tank, a flow path, an electrode, and the like) are independently provided for each sequencer constituting the array and these components should be integrated. However, PTL 2 only discloses that the components (the liquid tank, the electrode, and the like) are merely arranged in parallel, and such a configuration increases the array area, and as a result, it becomes a factor that inhibits integration and parallelization of the sequencer.

In addition, PTL 2 does not disclose any method of isolating the liquid tanks in parallel and a configuration of a wiring connected to each electrode at all. Therefore, with regard to the arraying of the solid-state type nanopore sequencers, a configuration enabling integration and parallelization of the sequencers is required.

Here, the present invention provides a technique of integrating and parallelizing a liquid tank, a flow path, an electrode, and the like in arraying of a solid-state type nanopore sequencer.

Solution to Problem

For example, in order to solve the above problem, the configuration described in the claims is adopted. This application includes a plurality of means for solving the above problem, and for example, there is provided a biological sample analysis chip including a first substrate, a membrane disposed on the first substrate, a first liquid tank which is provided with a first electrode, a plurality of second liquid tanks each of which is provided with at least one flow path and a second electrode, and a second substrate disposed below the first substrate, in which the plurality of second liquid tanks are substantially insulated from each other, the membrane disposed on the first substrate is disposed between the first liquid tank and the plurality of second liquid tanks so as to form a portion of the first liquid tank and a portion of the plurality of second liquid tanks, and the second substrate is provided with the at least one flow path and the second electrode so as to form a portion of the plurality of second liquid tanks.

Advantageous Effects of Invention

According to the present invention, it is possible to provide a technique of integrating and parallelizing a liquid tank, a flow path, an electrode, and the like in arraying of a solid-state type nanopore sequencer. Note that, features relating to the present invention will become apparent from the description of this specification and the accompanying drawings. Further, problems, configurations, and effects other than those described above will be clarified by the description of the following examples.

DESCRIPTION OF EMBODIMENTS

Hereinafter, examples of the present invention will be described below with reference to the drawings. Each drawing is schematically drawn, and a portion unnecessary for explanation is omitted. The structures, materials, and forming methods described in the examples are merely an example for embodying the concept of the present invention, and do not strictly specify the materials, dimensions, and the like.

Example 1

In the following description, an example of a biological sample analysis chip in the case where the number of arrays is two will be described. Of course, the number of arrays of the biological sample analysis chip may be two or more.

Figure 1:
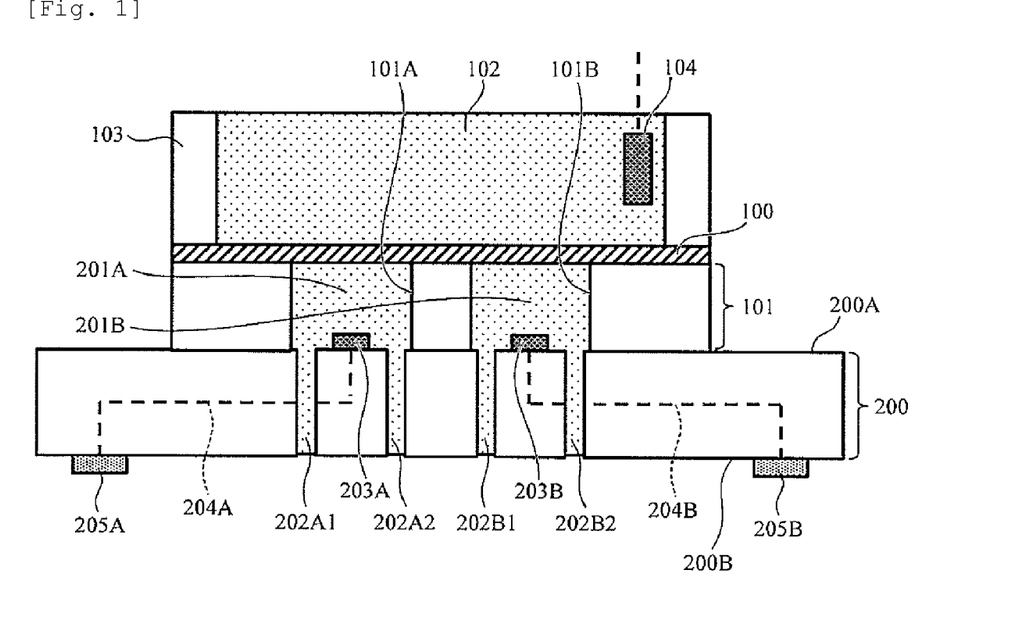
FIG. 1 is a schematic cross-sectional view of a main portion of a biological sample analysis chip in Example 1.

FIG. 1 is a schematic cross-sectional view of the biological sample analysis chip in Example 1. The biological sample analysis chip is formed of mainly a membrane 100, a first substrate 101, a support material 103, and a second substrate 200.

The biological sample analysis chip is further provided with a first liquid tank 102, a plurality of second liquid tanks 201A and 201B, a first electrode 104, a plurality of flow paths 202A1, 202A2, 202B1, and 202B2, a plurality of second electrodes 203A and 203B, a plurality of wirings 204A and 204B, and a plurality of external connection terminals 205A and 205B.

The membrane 100 is disposed on the first substrate 101. Further, the support material 103 is disposed on the first substrate 101. The first liquid tank 102 is a space disposed above the membrane 100. More specifically, the first liquid tank 102 is a space formed by the membrane 100 and the support material 103. The first electrode 104 is disposed in the first liquid tank 102.

The plurality of second liquid tanks 201A and 201B are spaces disposed below the membrane 100. More specifically, the plurality of second liquid tanks 201A and 201B are spaces formed of the membrane 100, the first substrate 101, and the second substrate 200. The first substrate 101 is provided with a plurality of opening portions 101A and 101B so as to form a portion of the plurality of second liquid tanks 201A and 201B. The spaces surrounded by the inner walls of the plurality of opening portions 101A and 101B, the membrane 100, a first surface 200A of the second substrate 200 are the plurality of second liquid tanks 201A and 201B.

As described above, the membrane 100 disposed on the first substrate 101 is disposed between the first liquid tank 102 and the plurality of second liquid tanks 201A and 201B so as to form a portion of the first liquid tank 102 and a portion of the plurality of second liquid tanks 201A and 201B.

Figure 2:
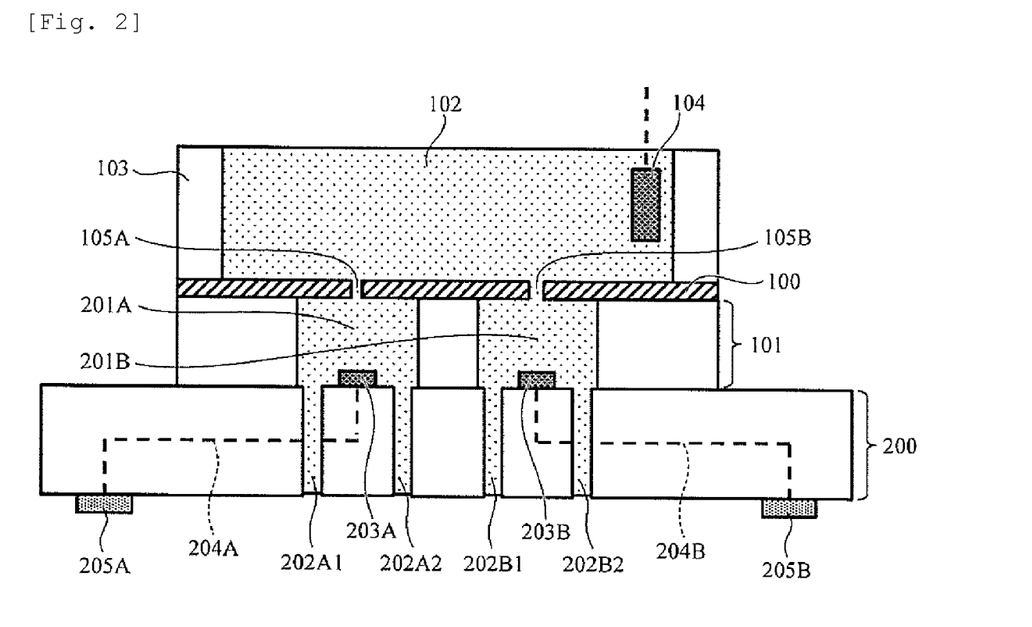
FIG. 2 is a schematic cross-sectional view of a main portion of the biological sample analysis chip in Example 1, and a diagram illustrating a state in which pores are formed in a membrane.

The membrane 100 includes a plurality of pores 105A and 105B. FIG. 1 illustrates a state before the pores 105A and 105 B are formed in the membrane 100, and FIG. 2 illustrates a state in which the pores 105A and 105B are formed in the membrane 100. In this example, the plurality of pores 105A and 105B are formed immediately before analysis. A method of forming the pores 105A and 105B will be described later. As another example, the pores 105A and 105B may be formed in advance in the membrane 100.

The membrane 100 is divided into a plurality of sections for each of the second liquid tanks 201A and 201B between the first liquid tank 102 and the second liquid tank 201A and 201B. In the present example, the two second liquid tanks 201A and 201B are provided for the first liquid tank 102, and thus the membrane 100 includes two sections. The membrane 100 includes pores 105A and 105B for each section. That is, the plurality of pores 105A and 105B are provided so as to correspond to the second liquid tanks 201A and 201B.

The second substrate 200 is disposed below the first substrate 101. In this example, the first substrate 101 and the second substrate 200 are in direct contact with each other. In this example, the second substrate 200 is formed of a printed board. The second substrate 200 may be a printed board having the insulating properties. Electrodes and wiring configurations which will be described below are formed on the surface of the second substrate 200 or the surface and the inside thereof.

The second substrate 200 is provided with a plurality of flow paths 202A1, 202A2, 202B1, and 202B2, a plurality of second electrodes 203A and 203B, a plurality of wirings 204A and 204B, and a plurality of external connection terminals 205A and 205B.

The plurality of flow paths 202A1, 202A2, 202B1, and 202B2 are through holes penetrating the second substrate 200. Two flow paths 202A1 and 202A2 are provided with respect to the second liquid tank 201A, and two flow paths 202B1 and 202B2 are provided with respect to the second liquid tank 201B. Note that, the flow paths 202A1, 202A2, 202B1, and 202B2 are not limited to this structure and may be formed in such a manner as to connect the outside and the second liquid tank. In this example, two flow paths are provided for each second liquid tank, but at least one flow path may be provided for one second liquid tank.

The second electrode 203A is disposed in the second liquid tank 201A, and is disposed on the first surface 200A of the second substrate 200. The second electrode 203B is disposed in the second liquid tank 201B, and is disposed on the first surface 200A of the second substrate 200.

The external connection terminal 205A is disposed on a second surface 200B on the side opposite to the first surface 200A on which the second electrode 203A is disposed. The external connection terminal 205A is connected to the second electrode 203A via the wiring 204A. In addition, the external connection terminal 205B is disposed on the second surface 200B on the side opposite to the first surface 200A on which the second electrode 203B is disposed. The external connection terminal 205B is connected to the second electrode 203B via the wiring 204B.

A procedure for preparing the biological sample analysis chip illustrated in FIGS. 1 and 2 will be described. First, the first substrate 101 is prepared and the silicon nitride film is provided on the first substrate 101. Next, the opening portions 101A and 101B are formed on the first substrate 101 from the back surface of the first substrate 101 by dry etching and wet etching. As a result, the membrane 100 of the silicon nitride film having a plurality of windows is formed.

Next, the second electrodes 203A and 203B, the wiring 204A connected to the second electrode 203A, the wiring 204B connected to the second electrode 203B, the external connection terminal 205A connected to the wiring 204A, the external connection terminal 205B connected to the wiring 204B, and the flow paths 202A1, 202A2, 202B1, and 202B2 are formed on the second substrate 200 by using a printed board multilayer wiring technology.

As one example, a glass epoxy substrate of the insulator is used for the second substrate 200. Copper is used for the wirings 204A and 204B. A metal via is formed in a vertically extending portion in which the plurality of layers of the second substrate 200 are connected to each other. For the external connection terminals 205A and 205B, a laminated film of copper and gold is used. The external connection terminals 205A and 205B are arranged in the outer periphery (here, the outer periphery of the second surface 200B) of the second substrate 200. The plurality of through holes are formed as the flow paths 202A1, 202A2, 202B1, and 202B2 on the second substrate 200. At this time, layout is performed so that the flow paths 202A1, 202A2, 202B1, and 202B2 do not overlap with the wirings 204A and 204B.

Figure 3:
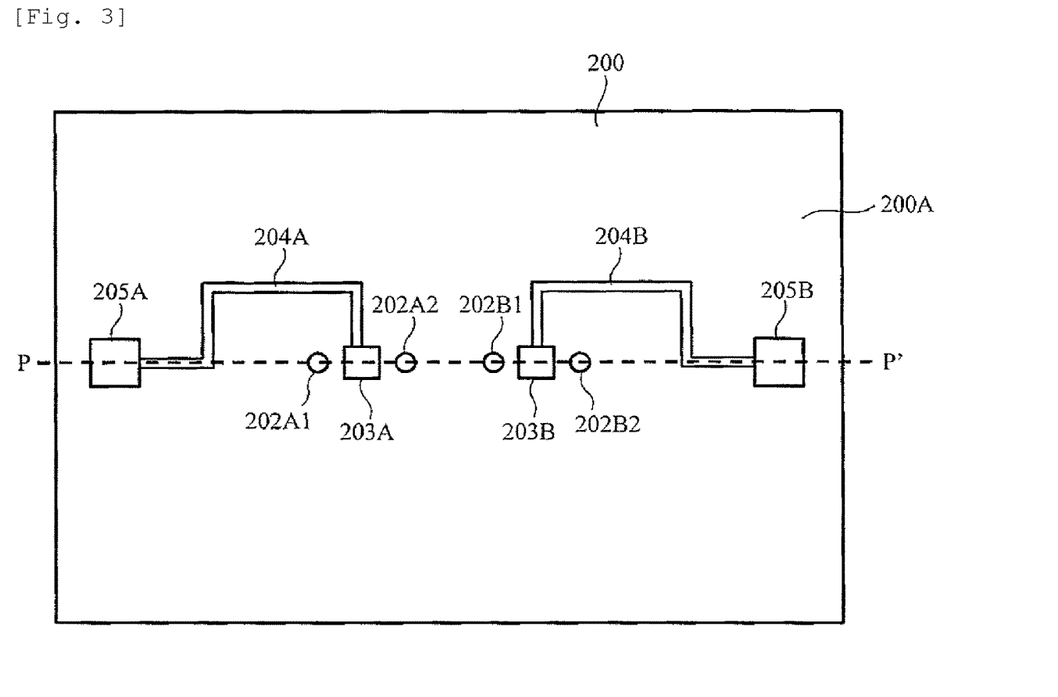
FIG. 3 is a plane layout diagram of a second substrate in Example 1.

FIG. 3 illustrates a portion (the second electrode, the wiring disposed in the horizontal direction, and the flow path) of the plane layout diagram of the second substrate 200 which is formed in the above procedure. Here, the second electrodes 203A and 203B are arranged on the surface layer (the first surface 200A) of the second substrate 200. Each of the wirings 204A and 204B is disposed in the inner layer of the second substrate 200. Although not shown in FIG. 3, each of the external connection terminals 205A and 205B is disposed on the surface layer (the second surface 200B on the side opposite to the first surface 200A) on the side opposite to the second substrate 200.

FIG. 1 illustrates a sectional view taken along line P-P' in FIG. 3. In FIG. 3, the second electrode 203A and the external connection terminal 205A are connected to each other via the wiring 204A, and the wiring 204A is formed so as to bypass the flow paths 202A1 and 202A2 (the wiring 204A and the flow paths 202A1 and 202A2 are not connected). Similarly, the second electrode 203B and the external connection terminal 205B are connected to each other via the wiring 204B, and the wiring 204B is formed so as to bypass the flow paths 202B1 and 202B2 (the wiring 204B and the flow paths 202B1 and 202B2 are not connected).

The description returns to FIG. 1. For the second electrodes 203A and 203B, a silver-silver chloride paste having good potential stability is used. The end portions of the wirings 204A and 204B are covered with the paste so as to form the second electrodes 203A and 203B. Thereafter, the first substrate 101 and the second substrate 200 formed in the above procedure are coupled (combined) using a clamp.

The second liquid tanks 201A and 201B are constituted by the spaces formed of the membrane 100, the first substrate 101, and the second substrate 200. The second liquid tank 201A and the second liquid tank 201B are constituted as independent spaces by the first substrate 101 and the second substrate 200, respectively, and the second liquid tank 201A and the second liquid tank 201B are substantially insulated from each other. Here, the term "substantially insulated" means that when performing analysis using the biological sample analysis chip described in this example, a resistance value between the second liquid tank 201A and the second liquid tank 201B is larger than a resistance value occurring in the pores 105A and 105B in a nanometer order to be opened to the membrane 100, and the second liquid tank 201A and the second liquid tank 201B are insulated from each other to a level that does not hinder the measurement of the current value flowing through the pores 105A and 105B.

When the first substrate 101 and the second substrate 200 are coupled to each other using the clamp, the second electrode 203A is disposed in the second liquid tank 201A. Further, the flow paths 202A1 and 202A2 are connected to the second liquid tank 201A. Similarly, the second electrode 203B is disposed in the second liquid tank 201B. In addition, the flow paths 202B1 and 202B2 are connected to the second liquid tank 201B.

Next, a wall-shaped support material 103 is attached onto the first substrate 101, and thereby the first liquid tank 102 is formed. In this example, the first liquid tank 102 is a common liquid tank with respect to the second liquid tanks 201A and 201B. In addition, the first electrode 104 is introduced to the first liquid tank 102. The first electrode 104 is a silver-silver chloride bar.

Then, the first liquid tank 102, the second liquid tanks 201A, and 201B are filled with an electrolyte solution so as to bring both surfaces of the membrane 100 into contact with the electrolyte solution. The solution is introduced to the second liquid tank 201A from the flow path 202A1 or the flow path 202A2. Further, the solution is introduced to the second liquid tank 201B from the flow path 202B1 or the flow path 202B2.

Thereafter, a voltage is applied between the first electrode 104 and the second electrodes 203A and 203B. With this, nanometer-sized pores 105A and 105B are formed in the membrane 100. More specifically, following the filling of the solution, the first electrode 104 is grounded and a pulsed voltage is applied between the second electrodes 203A and 203B. The nanometer-sized pores 105A and 105B are formed in the membrane 100 by an insulation breakdown mechanism. The diameters of the pores 105A and 105B become larger as the current value flowing through the pores 105A and 105B is larger, and thus are controlled by the current value (refer to Itaru Yanagi et al., Sci. Rep. 4, 5000 (2014), and WO2015/097765).

Through the above procedure, the biological sample analysis chip in a case illustrated in FIG. 1 where the number of arrays is two is realized. By using this method, it is possible to integrate the liquid tank, the flow path, the electrode, and the wiring.

The biological sample analysis chip of this example is provided with the first substrate 101 including the membrane 100, and the second substrate 200 in which the plurality of through holes (flow paths 202A1, 202A2, 202B1, and 202B2), and the plurality of second electrodes 203A and 203B are arranged in an array. In addition, the wirings 204A and 204B connected to the plurality of second electrodes 203A and 203B, and the plurality of external connection terminals 205A and 205B are provided on the second substrate 200. With such a configuration, it is possible to realize integration and parallelization of the liquid tank, the flow path, the electrode, and the wiring in arraying the solid-state type nanopore sequencer.

Further, in a case where the second substrate 200 is formed of a printed board of an insulator, the second liquid tanks 201A and 201B can be insulated only by configuring the flow paths 202A1, 202A2, 202B1, and 202B2 as the through holes of the second substrate 200.

In addition, by forming the second substrate 200 using the multilayer wiring technology, even in a case where the array scale is expanded, it is possible to extract the wiring from each of the second electrodes 203A and 203B to the outside.

The above is the procedure for preparing the biological sample analysis chip according to this example, but the effectiveness of the invention is not limited to this case. For example, the silicon nitride film is used for the membrane 100, but a silicon oxide film, graphene, graphite, an organic material, a polymer material, or the like may be used for the membrane 100.

A silver-silver chloride electrode was used as the electrode of this example, other metal such as platinum, gold, or the like may be used as a material of the electrode. In addition, the glass epoxy was used for the second substrate 200, other insulators such as Teflon may be used.

In this example, the support material 103 of the first liquid tank 102 has a wall shape, and a large opening portion is provided in the upper portion of the first liquid tank 102, but the invention is not limited to this configuration. For example, the first liquid tank 102 may have another configuration such as a configuration having a ceiling, or a configuration in which the support material 103 of the first liquid tank 102 is provided on the second substrate 200.

In this example, the pores 105A and 105B are formed by applying a voltage to the membrane 100, but the present invention is not limited thereto. The pores 105A and 105B may be formed by other methods such as irradiating the membrane 100 with an electron beam (refer to A. J. Storm et al., Nat. Mat. 2 (2003)).

In this example, the first substrate 101 and the second substrate 200 are combined with each other by clamping, but the first substrate 101 and the second substrate 200 may be directly bonded to each other.

Example 2

Figure 4:
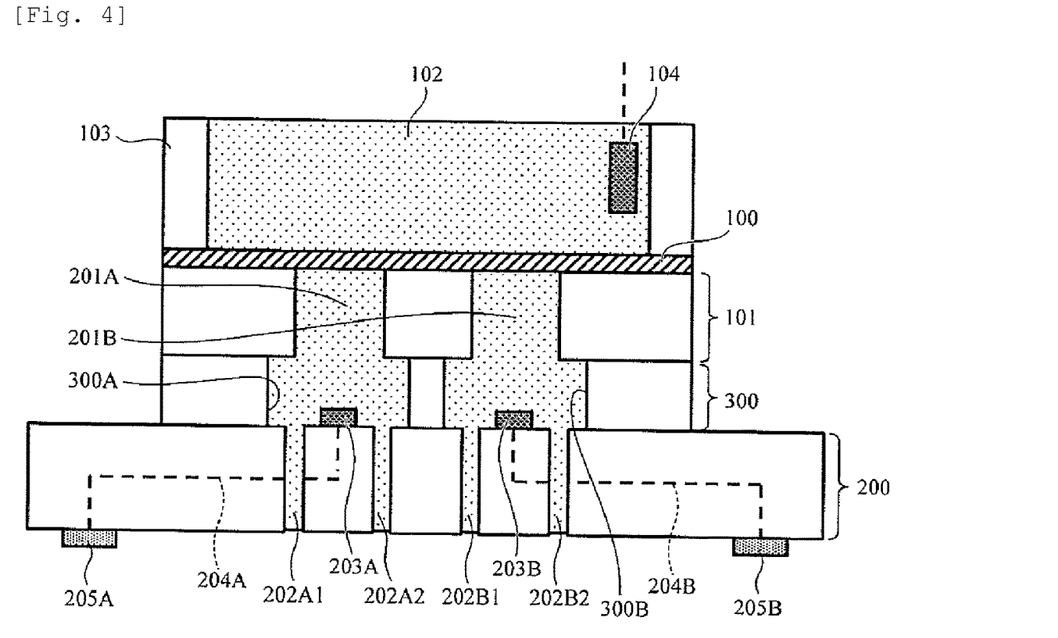
FIG. 4 is a schematic cross-sectional view of a main portion of a biological sample analysis chip in Example 2.

FIG. 4 illustrates a schematic cross-sectional view of the biological sample analysis chip in Example 2, and a schematic cross-sectional view of the biological sample analysis chip having a configuration in which an insulating layer is interposed between the first substrate 101 and the second substrate 200. Components described in the above-described Example 1 are denoted by the same reference numerals, and description thereof will not be repeated.

In this example, an insulating layer 300 is disposed between the first substrate 101 and the second substrate 200. As such, the first substrate 101 may be disposed on the second substrate 200 via the insulating layer 300.

Hereinafter, only the points different from the forming procedure of the Example 1 will be described. The second electrodes 203A and 203B, the wirings 204A and 204B, the external connection terminals 205A and 205B, and the flow paths 202A1, 202A2, 202B1, and 202B2 are formed on the second substrate 200 by using the printed board wiring technology. Thereafter, the patterned insulating layer 300 is formed on the second substrate 200. The insulating layer 300 is provided with a plurality of opening portions 300A and 300B so as to correspond to the plurality of second liquid tanks 201A and 201B. Here, a resin is used for the insulating layer 300. Thereafter, the first substrate 101 on which the membrane 100 is formed is adhered onto the insulating layer 300.

In this example, the insulating layer 300 constitutes a portion of the plurality of second liquid tanks 201A and 201B. The plurality of second liquid tanks 201A and 201B are spaces formed of the membrane 100, the first substrate 101, the insulating layer 300, and the second substrate 200.

Through the above procedure, the biological sample analysis chip in a case illustrated in FIG. 4 where the number of arrays is two is realized. As compared with Example 1, a mechanism for clamping the first substrate 101 and the second substrate 200 is not necessary, and thus handling becomes simple. Note that, the insulating layer 300 may be patterned after being formed on the second substrate 200.

Example 3

Figure 5:
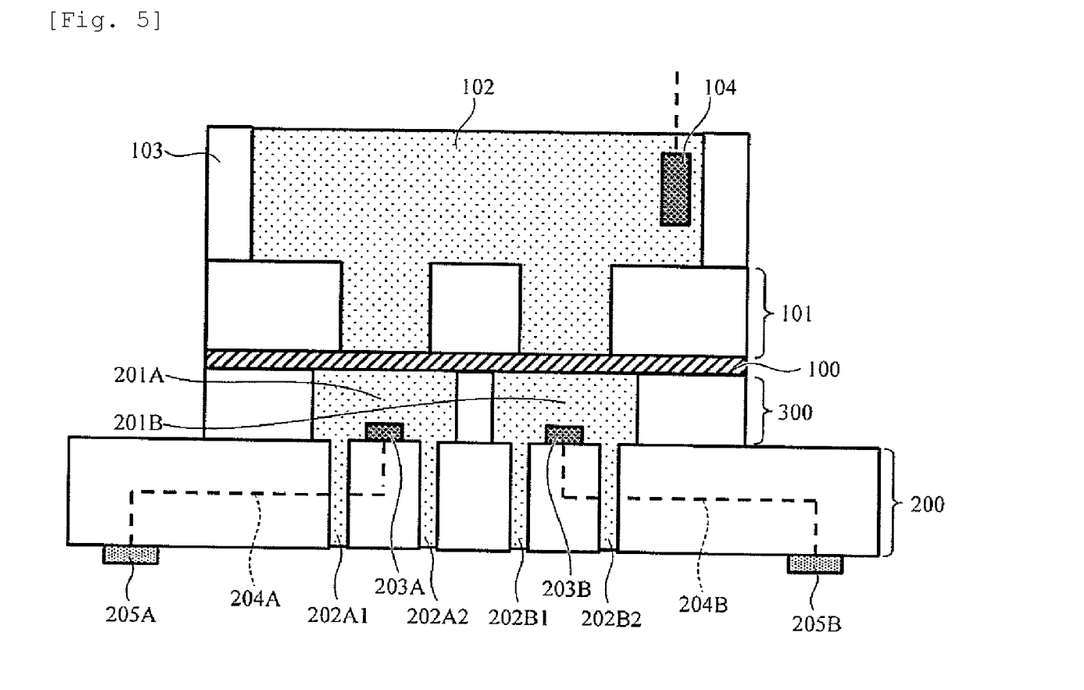
FIG. 5 is a schematic cross-sectional view of a main portion of a biological sample analysis chip in Example 3.

FIG. 5 is a schematic cross-sectional view of the biological sample analysis chip in Example 3. In the above example, the surface of the first substrate 101 on the side opposite to the side on which the membrane 100 is formed is brought into contact with the second substrate 200; however, in this example, the surface of the first substrate 101 on the side on which the membrane 100 is formed is disposed on the second substrate 200 side.

Hereinafter, only the points different from the forming procedure of the Example 2 will be described. The second electrodes 203A and 203B, the wirings 204A and 204B, the external connection terminals 205A and 205B, and the flow paths 202A1, 202A2, 202B1, and 202B2 are formed on the second substrate 200 by using the printed board wiring technology. Thereafter, the patterned insulating layer 300 is formed on the second substrate 200. A resin is used for the insulating layer 300. Then, the insulating layer 300 is adhered to the first substrate 101 provided with the membrane 100 in a state where the surface on which the membrane 100 is formed is positioned on the lower side of the first substrate 101.

In this example, the first substrate 101 constitutes a portion of the first liquid tank 102. The first liquid tank 102 is a space formed by the membrane 100, the first substrate 101, and the support material 103. Further, the plurality of second liquid tanks 201A and 201B are spaces formed by the membrane 100, the insulating layer 300, and the second substrate 200.

Through the above procedure, the biological sample analysis chip in a case illustrated in FIG. 5 where the number of arrays is two is realized. Note that, the insulating layer 300 may be patterned after being formed on the second substrate 200.

Example 4

Figure 6:
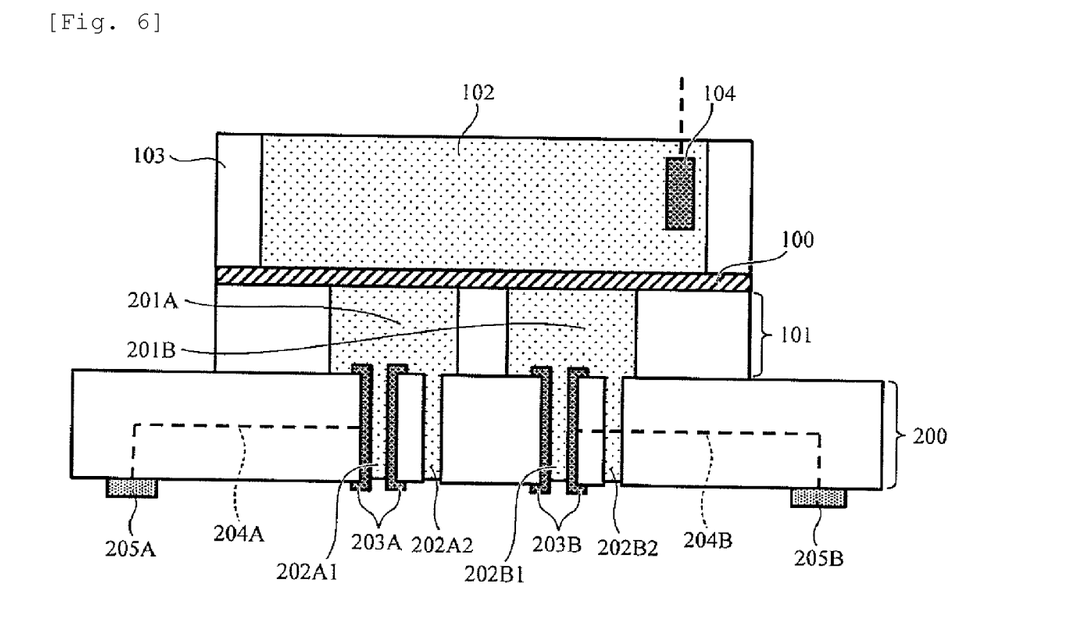
FIG. 6 is a schematic cross-sectional view of a main portion of a biological sample analysis chip in Example 4.

FIG. 6 is a schematic cross-sectional view of the biological sample analysis chip in Example 4. In the wirings 204A and 204B of the above Examples 1 to 3, the metal via is formed in the vertically extending portion in which the plurality of layers of the second substrate 200 are connected to each other. On the other hand, in this example, the vertically extending portion in which the plurality of layers of the second substrate 200 are connected to each other is formed by a plated through hole method.

Hereinafter, only the points different from the forming procedure of the Example 1 will be described. The external connection terminals 205A and 205B and the wirings 204A and 204B are formed by using the printed board wiring technology. Thereafter, the through holes are formed in the areas of the flow paths 202A1 and 202B1, and with this, a portion of the wirings 204A and 204B is exposed to the wall surfaces of the flow paths 202A1 and 202B1.

A metal film is disposed on the inner wall of the through hole. As one example, the inner wall of the through hole is subjected to copper plating and gold plating. Apart on which the metal plating is performed is used as a portion of the second electrodes 203A and 203B. With this, each of the second electrodes 203A and 203B is connected to each of the wirings 204A and 204B. After that, two through holes are separately formed on the second substrate 200. These through holes are used as the flow paths 202A2 and 202B2.

Through the above procedure, the biological sample analysis chip in a case illustrated in FIG. 6 where the number of arrays is two is realized. As compared with other examples, there is an effect that the area of the vias can be suppressed. Note that, since the second electrodes 203A and 203B are formed on the inner wall of the through hole, an electrode material which can be formed on the inner wall of the through hole and which has good coverage may be adopted in this example.

Further, this example can be applied to Examples 2 and 3 in which the insulating layer 300 is provided. In this case, after the procedure for forming the above-described through hole, the patterned insulating layer 300 is formed on the second substrate 200.

Example 5

Figure 7:
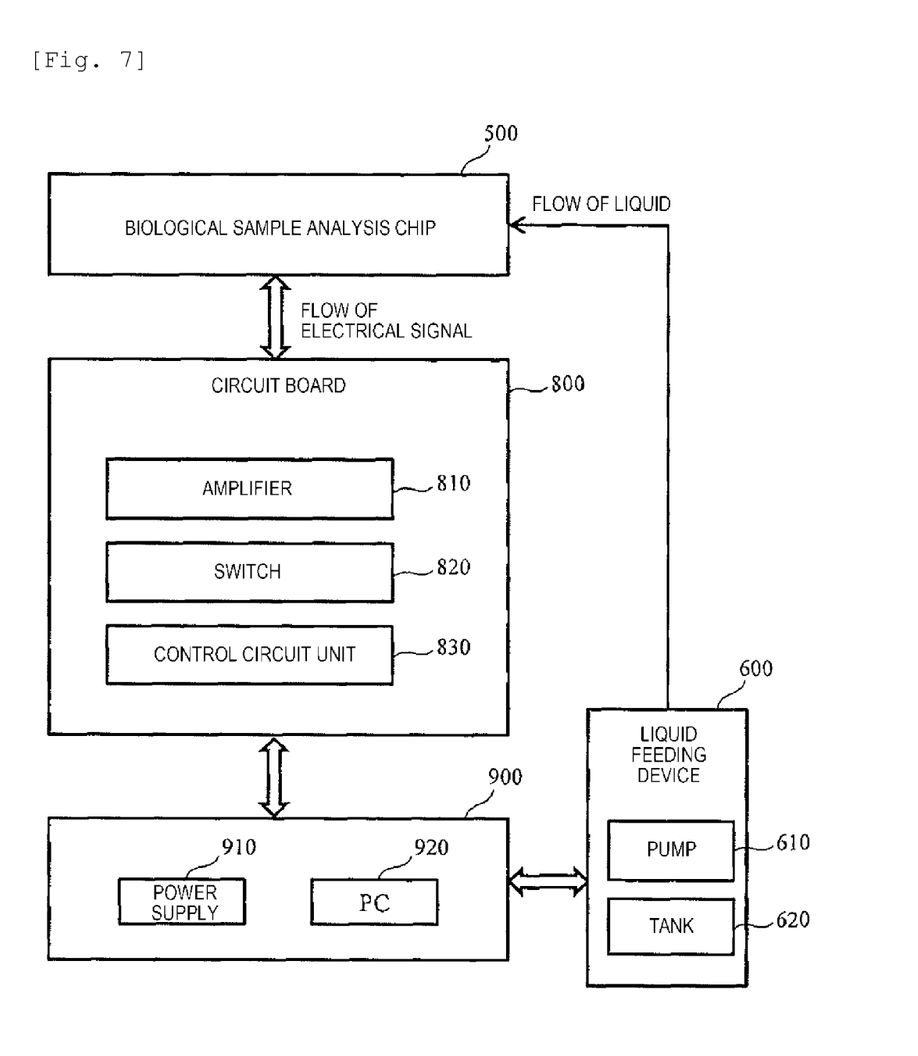
FIG. 7 is a block diagram of a main portion illustrating a biological sample analyzer in Example 5.
Figure 8:
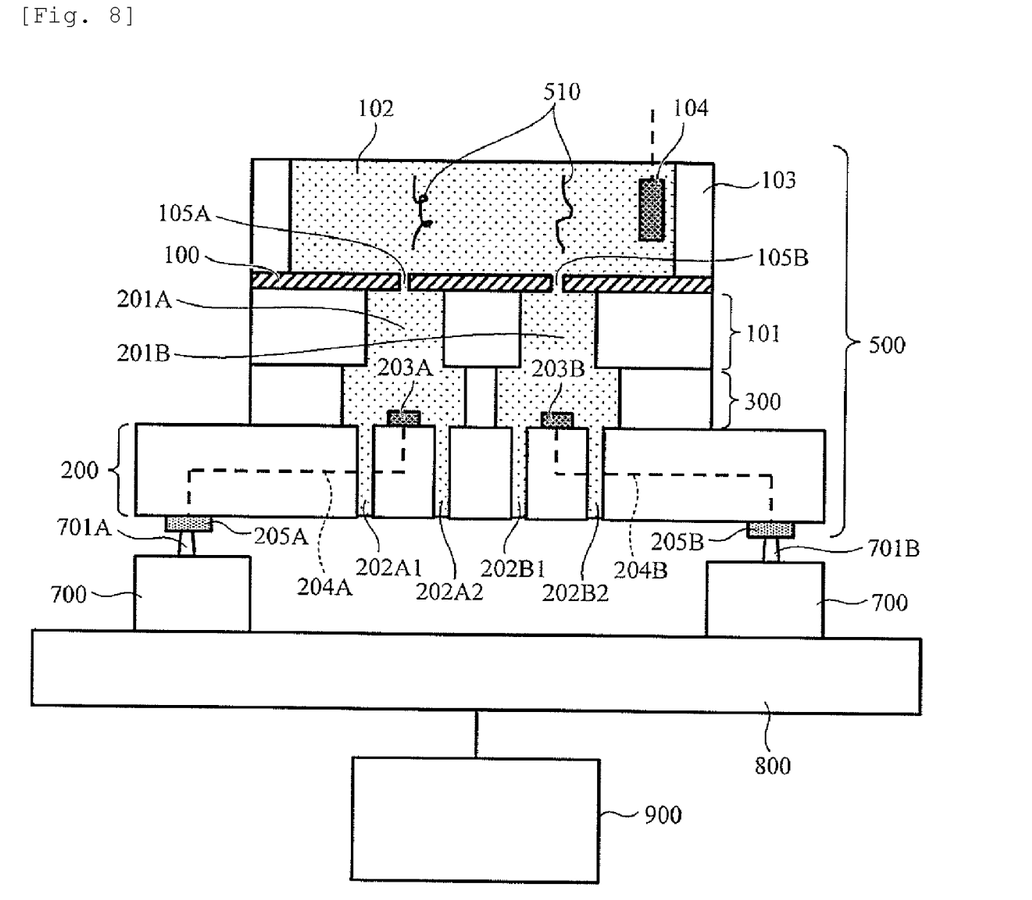
FIG. 8 is a schematic cross-sectional view of a main portion illustrating the biological sample analyzer in Example 5.

Hereinafter, examples of a biological sample analyzer and a biological sample analysis method using the biological sample analysis chip described in Examples 1 to 4 will be described. FIG. 7 is a block diagram illustrating a biological sample analyzer in Example 5, and FIG. 8 is a schematic cross-sectional view of the biological sample analyzer.

The biological sample analyzer is provided with a biological sample analysis chip 500, a liquid feeding device 600, a circuit board (control circuit) 800, and a power supply and control unit 900.

The biological sample analysis chip 500 corresponds to the biological sample analysis chip in Examples 1 to 4. FIG. 8 illustrates the biological sample analysis chip corresponding to Example 2 as one example.

The circuit board 800 is provided with an amplifier 810, a switch 820, and a control circuit portion 830 such as an analog to digital conversion circuit, and controls the sequence of the biological sample analysis. The power supply and control unit 900 is provided with a power supply 910 and a personal computer (PC) 920. The power supply and control unit 900 is connected to the liquid feeding device 600 and the circuit board 800.

The power supply 910 is used for applying the voltage between the first electrode 104 and the second electrodes 203A and 203B. The circuit board 800 independently controls the voltage between the first electrode 104 and the second electrodes 203A and 203B. The PC 920 controls the power supply 910 and each component of the analyzer and controls the entire analyzer (control of liquid supply, supply of power to the circuit board 800, input of measurement start, or the like). In addition, the PC 920 also has a function of a measuring unit that independently measures the current value between the first electrode 104 and the second electrodes 203A and 203B.

The PC 920 is provided with at least a processor such as a central processing unit (CPU), a memory, and a storage unit such as a hard disk. The PC 920 measures a voltage applied between the first electrode 104 and the second electrodes 203A and 203B, and the current value between the first electrode 104 and the second electrodes 203A and 203B (a change of the current value when the biological sample passes through the pores 105A and 105B), and records the measurement in a storage unit. The PC 920 detects the structural features of the biological sample by using the measured current value.

The example of FIG. 7 is an example, and the configuration is not limited to this example. For example, the analog to digital conversion circuit of the circuit board 800 may be disposed in the power supply and control unit 900, and the device variations are varied. A system suitable for the measurement environment may be constructed.

The liquid feeding device 600 is provided with a pump 610 and a tank 620, and supplies the solution to the first liquid tank 102 and the second liquid tanks 201A and 201B of the biological sample analysis chip 500. Control of the amount of liquid in the liquid feeding device 600 and timing for supplying the solution are controlled by the power supply and control unit 900.

In order to lower the operation cost of the apparatus, it is preferable that the biological sample analysis chip 500 has a disposable configuration, and the biological sample analysis chip 500 is configured to be detachable to a previously prepared circuit board 800.

FIG. 8 illustrates a mechanism in which the biological sample analysis chip 500 is configured to be detachable from the circuit board 800. As a removing mechanism, the circuit board 800 is provided with a socket 700. The socket 700 is provided with metal pins (connecting portions) 701A and 701B having metal protrusions. The metal pin 701A can be electrically connected to the external connection terminal 205A, and the metal pin 701B can be electrically connected to the external connection terminal 205B. In addition, the metal pins 701A and 701B can repeat contact and non-contact with the external connection terminals 205A and 205B.

The external connection terminals 205A and 205B can be connected to the circuit board 800 via the metal pins 701A and 701B, and can be connected to the power supply and control unit 900 via the circuit board 800. As a result, a voltage can be applied to the biological sample analysis chip 500 from the power supply 910 of the power supply and control unit 900. In a case where the biological sample analysis chip 500 is disposable, the metal pins 701A and 701B can repeat contact and non-contact with the external connection terminals 205A and 205B. Therefore, it is possible to replace the biological sample analysis chip 500.

According to this configuration, the analysis can be performed by disposing the biological sample analysis chip 500 on the socket 700 of the circuit board 800. In this configuration, soldering is not necessary, and attachment and detachment of the biological sample analysis chip 500 can be repeated.

An example of analyzing a biological sample using the biological sample analyzer of this example will be described. First, the first liquid tank 102, and the second liquid tanks 201A and 201B are filled with the electrolyte solution so as to bring both surfaces of the membrane 100 into contact with the electrolyte solution. A solution is introduced to the second liquid tank 201A via the flow path 202A1 or the flow path 202A2, and a solution is introduced to the second liquid tank 201B from the flow path 202B1 or the flow path 202B2. The biological sample analyzer may be provided with a solution supply nozzle which is connected to the pump 610 of the liquid feeding device 600 as a mechanism for introducing the solution. The solution supply nozzle has a configuration that can be inserted into the flow paths 202A1, 202A2, 202B1, and 202B2.

The solution supply nozzle may be disposed in the vicinity of the end portions of the flow paths 202A1, 202A2, 202B1, and 202B2. In addition, the solution supply nozzle may be configured to be inserted into the end portions of the flow paths 202A1, 202A2, 202B1, and 202B2, or configured to come into contact with end portions of the flow paths 202A1, 202A2, 202B1, and 202B2, for example.

Figure 9:
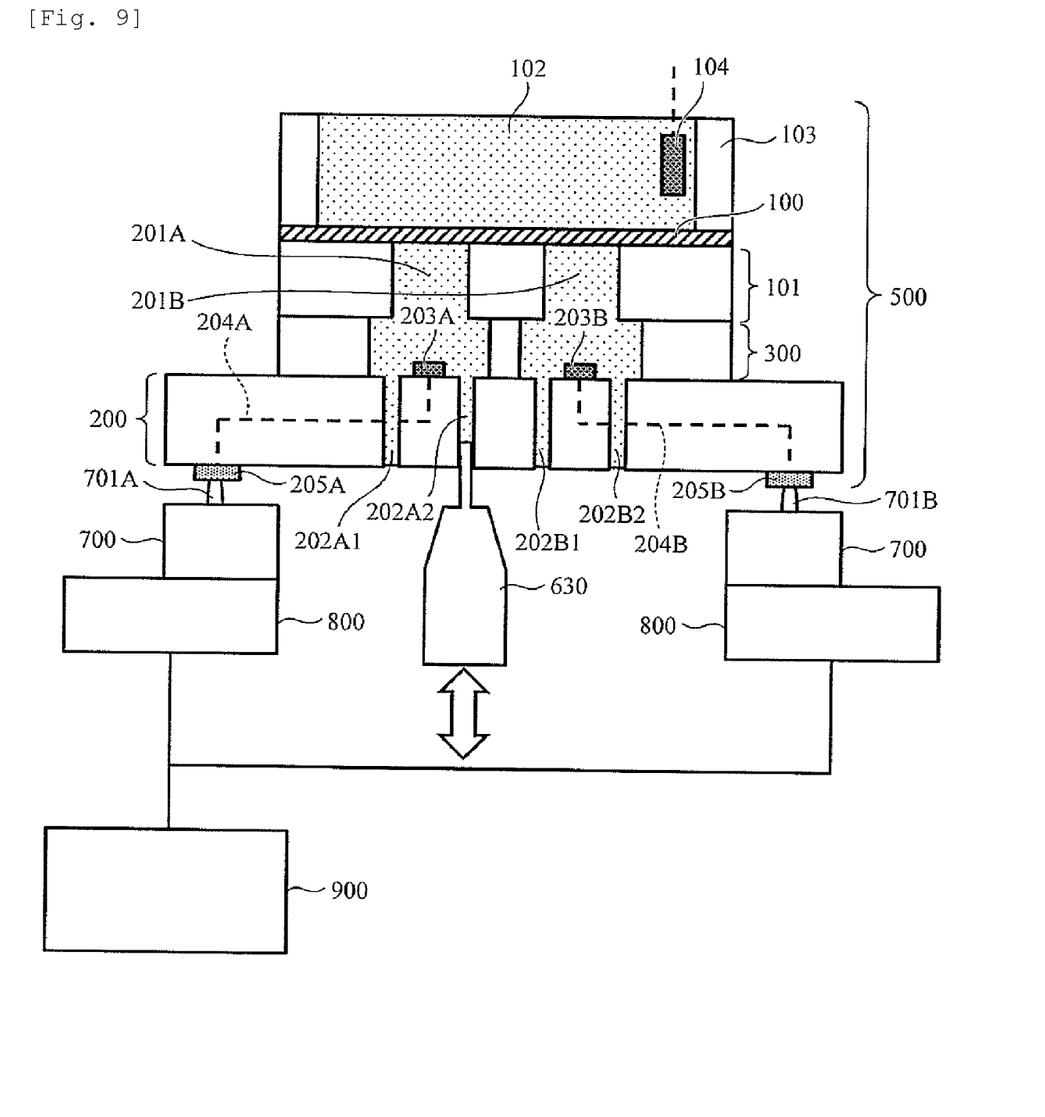
FIG. 9 is a schematic cross-sectional view of one example of the biological sample analyzer having a solution supply nozzle in Example 5.

FIG. 9 is a schematic cross-sectional view of the biological sample analyzer having a solution supply nozzle. In this example, the circuit board 800 has an opening portion in a center portion thereof. According to this configuration, since the hollow portion is provided under the biological sample analysis chip 500, a solution supply nozzle 630 can be inserted into the flow paths 202A1, 202A2, 202B1, and 202B2 via the hollow portion.

The description returns to FIG. 8. After the above-described procedure, a biological sample 510 is introduced to the first liquid tank 102. After that, voltages are independently applied to the second electrodes 203A and 203B by using the power supply and control unit 900 and the circuit board 800. With this, the biological sample 510 passes through the pores 105A and 105B. When the voltage is applied, an electric field is generated around the pores 105A and 105B, and electrophoresis force is generated such that the biological sample 510 charged in the liquid is attracted to the electric field. The movement of the biological sample 510 is controlled by this electrophoretic force. Here, the current value to be measured is changed between before the biological sample 510 passes through the pores 105A and 105B, and when the biological sample 510 is passing through the pores 105A and 105B. The reason for this is that the pores 105A and 105B are partially blocked by the sectional area of the biological sample 510 and the resistance values of the pores 105A and 105B are changed. The PC 920 of the power supply and control unit 900 independently detects and records the change in the current value generated in each of the pores 105A and 105B in parallel.

Through the above procedure, the biological sample analysis method in a case where the number of arrays is two is realized. By using this method, it is possible to measure arrayed biological sample analysis chips in parallel and to improve analysis throughput. However, the effectiveness of the present invention is not limited to this case. For example, in this example, the movement of the biological sample 510 is controlled only by the electrophoretic force, but it is also possible to control the movement of the biological sample 510 using a driving mechanism.

Figure 10:
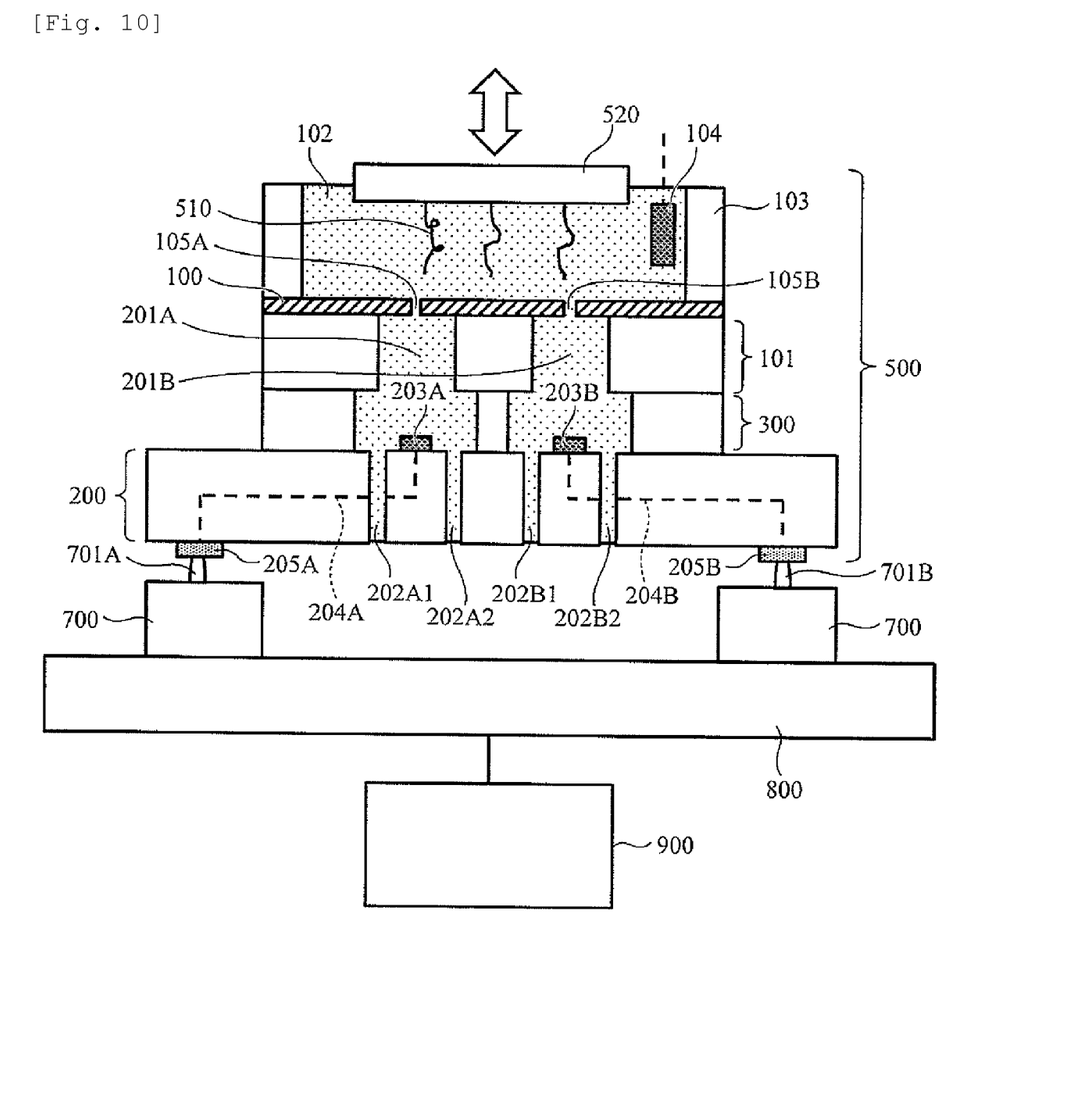
FIG. 10 is a schematic cross-sectional view of one example of the biological sample analyzer having a driving mechanism in Example 5.

FIG. 10 illustrates a schematic cross-sectional view of the biological sample analyzer having the driving mechanism. Only the differences from the apparatus configuration and analysis method of the above examples will be described below. The biological sample analyzer is further provided with a driving mechanism 520 that fixes the biological sample, and controls a distance between the membrane 100 and the biological sample 510. For example, in order to realize the above function, the driving mechanism 520 may include a motor and a piezo element.

The analysis method will be described. After the pores 105A and 105B are formed in the membrane 100 by the method described in the above example, the biological sample 510 fixed to the driving mechanism 520 is introduced to the first liquid tank 102. By moving the driving mechanism 520 toward the membrane 100, the biological sample 510 is caused to pass through the pores 105A and 105B. In addition, voltages are independently applied to the second electrodes the second electrodes 203A and 203B by using the power supply and control unit 900 and the circuit board 800. Here, the pores 105A and 105B are partially blocked by the sectional area of the biological sample 510 and the resistance values of the pores 105A and 105B are changed. The PC 920 of the power supply and control unit 900 independently detects and records the change in the current value generated in each of the pores 105A and 105B in parallel. According to this configuration, the speed at which the biological sample 510 passes through the pores 105A and 105B can be easily controlled, and thereby the reading accuracy can be improved.

According to the above Examples 1 to 5, it is possible to integrate the liquid tank, the flow path, the electrode, and the wiring in arraying the solid-state type nanopore sequencer. In addition, it is possible to perform measurement by a plurality of sequencers independently and in parallel, and it is possible to improve the analysis throughput.

The present invention is not limited to the examples described above, but includes various modifications. The above examples have been described in detail in order to explain the invention in an easy-to-understand manner, and are not necessarily limited to those having all the configurations described. Further, apart of the configuration of an example can be replaced by the configuration of another example. Further, a part of the configuration of another example can be added to the configuration of an example. Further, regarding a part of the configuration of each example, other configurations can be added, deleted, or replaced.

The function, the processing unit, and the like of the measuring unit may be realized by software by interpreting and executing a program that realizes the respective functions by the processor. Information such as programs, tables, files, and the like that realize each function can be stored in various types of non-transitory computer readable medium. As the non-transitory computer readable medium, for example, a flexible disk, a CD-ROM, a DVD-ROM, a hard disk, an optical disk, a magneto-optical disk, a CD-R, a magnetic tape, a nonvolatile memory card, a ROM and the like are used. Further, the function, the processing unit, and the like of the measuring unit may be realized by hardware, for example, by designing some or all of them with an integrated circuit or the like.

In the above examples, control lines and information lines indicate those which are considered to be necessary for explanation, and all the control lines and information lines for a product are not necessarily indicated. All the configurations may be mutually connected.

REFERENCE SIGNS LIST

100: MEMBRANE
101: FIRST SUBSTRATE
102: FIRST LIQUID TANK
103: SUPPORT MATERIAL
104: FIRST ELECTRODE
105A, 105B: PORE
200: SECOND SUBSTRATE
201A, 201B: SECOND LIQUID TANK
202A1, 202A2, 202B1, 202B2: FLOW PATH
203A, 203B: SECOND ELECTRODE
204A, 204B: WIRING
205A, 205B: EXTERNAL CONNECTION TERMINAL
300: INSULATING LAYER
500: BIOLOGICAL SAMPLE ANALYSIS CHIP
510: BIOLOGICAL SAMPLE
520: DRIVING MECHANISM
600: LIQUID FEEDING DEVICE
800: CIRCUIT BOARD
900: POWER SUPPLY AND CONTROL UNIT

The invention claimed is:

1. A biological sample analysis chip comprising:
a first substrate;
a membrane disposed on the first substrate;
a first liquid tank which is provided with a first electrode;
a plurality of second liquid tanks each of which is provided with a second electrode;
a second substrate disposed below the first substrate; and
at least one flow path disposed entirely within the second substrate,
wherein the plurality of second liquid tanks are substantially insulated from each other,
wherein the membrane disposed on the first substrate is disposed between the first liquid tank and the plurality of second liquid tanks so as to form a portion of the first liquid tank and a portion of the plurality of second liquid tanks,
wherein the second substrate is provided with a plurality of wirings connected to ach of the second electrode and a plurality of external connection terminals connected to the plurality of wirings,
wherein a first surface of the second substrate facing the membrane forms a portion of the plurality of second liquid tanks,
wherein the at least one flow path disposed entirely within the second substrate extends linearly in a direction intersecting the first surface from the first surface, as an upper boundary, to a second surface of the second substrate opposite to the first surface, as a lower boundary,
wherein the plurality of external connection terminals are arranged in an outer periphery of the second surface of the second substrate, and
wherein the second electrode is disposed above the at least one flow path and is disposed on the first surface of the second substrate.

2. The biological sample analysis chip according to claim 1, wherein
the membrane is provided with a plurality of pores respectively corresponding to each of the plurality of second liquid tanks.

3. The biological sample analysis chip according to claim 1, wherein
the at least one flow path is formed of a through hole penetrating the second substrate.

4. The biological sample analysis chip according to claim 1, wherein
the plurality of wirings include a metal via disposed inside the second substrate.

5. The biological sample analysis chip according to claim 1, wherein
the second substrate is formed of a printed board having insulating properties.

6. The biological sample analysis chip according to claim 1, wherein
the first substrate is disposed directly on the second substrate.

7. The biological sample analysis chip according to claim 1, further comprising:
a support material disposed on the first substrate, wherein the support material constitutes a portion of the first liquid tank.

* * * * *